(12) United States Patent
Sarakinos et al.

(10) Patent No.: US 8,420,683 B2
(45) Date of Patent: Apr. 16, 2013

(54) 5 SUBSTITUTED HYDANTOINS

(75) Inventors: Georgios Sarakinos, Munich (DE); Wilhelmus Hubertus Joseph Boesten, Sittard (NL); Dennis Heemskerk, Schinveld (NL); Ben De Lange, Munstergeleen (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 591 days.

(21) Appl. No.: 12/601,304

(22) PCT Filed: Jun. 3, 2008

(86) PCT No.: PCT/EP2008/056841
§ 371 (c)(1),
(2), (4) Date: Jan. 25, 2010

(87) PCT Pub. No.: WO2008/148755
PCT Pub. Date: Dec. 11, 2008

(65) Prior Publication Data
US 2010/0174092 A1    Jul. 8, 2010

(30) Foreign Application Priority Data
Jun. 6, 2007 (EP) .................................. 07109684

(51) Int. Cl.
*A61K 31/4166* (2006.01)
*C07D 233/76* (2006.01)

(52) U.S. Cl.
USPC ...................................... 514/389; 548/317.1

(58) Field of Classification Search ............... 548/317.1; 514/389
See application file for complete search history.

(56) References Cited

FOREIGN PATENT DOCUMENTS

| EP | 0 625 571 | 11/1994 |
|---|---|---|
| EP | 1 279 665 | 1/2003 |
| WO | 2005/108366 | 11/2005 |
| WO | 2008/067981 | 6/2008 |
| WO | WO-2008/067981 A2 * | 6/2008 |

OTHER PUBLICATIONS

U.S. Appl. No. 12/517,504, commonly assigned.*
Wessels, F.L. et al, Journal of Pharmaceutical Sciences, vol. 69 (9), Sep. 1980, pp. 1102-1104.*
International Search Report for PCT/EP2008/056841, mailed Dec. 16, 2008.
Yokozeki et al., "Mechanism of Asymmetric Production of D-Amino Acids from the Corresponding Hydantoins by Pseudomonas sp", Agric. Biol. Chem., vol. 51, No. 3, 1987, pages 721-728, XP002232803.

* cited by examiner

*Primary Examiner* — Kamal Saeed
*Assistant Examiner* — Janet L Coppins
(74) *Attorney, Agent, or Firm* — Nixon & Vanderhye P.C.

(57) ABSTRACT

The present invention relates to 5-substituted hydantoins, a process for the preparation of 5-substituted hydantoins and the use of 5-substituted hydantoins in the preparation of enantiomerically enriched α-amino acids. Furthermore, the present invention relates to the preparation of pharmaceutically active products such as perindopril and ramipril using the novel 5-substituted hydantoins.

10 Claims, No Drawings

5 SUBSTITUTED HYDANTOINS

This application is the U.S. national phase of International Application No. PCT/EP2008/056841, filed 3 Jun. 2008, which designated the U.S. and claims priority to European Application No. 07109684.6, filed 6 Jun. 2007, the entire contents of each of which are hereby incorporated by reference.

FIELD OF THE INVENTION

The present invention relates to 5-substituted hydantoins, a process for the preparation of 5-substituted hydantoins and the use of 5-substituted hydantoins in the preparation of enantiomerically enriched α-amino acids.

BACKGROUND

Hydantoins (imidazolidine-2,4-diones) substituted at the 5-position, having the general formula [1], form a class of compounds that is known for almost 135 years after the first disclosure of 5-methylhydantoin ([1], $R_1=R_2=R_3=H$) by Urech (Ann., 165, 99 (1873)).

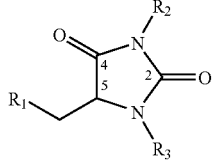

[1]

Today, 5-substituted hydantoins are versatile building blocks in many synthetic approaches towards a wide variety of medicines and some, like the anticonvulsant 5,5-diphenylhydantoin, have therapeutic properties themselves. One particularly attractive application is the use of hydantoins in multi-enzyme mediated synthesis of enantiomerically pure α-amino acids. For instance, WO 2001/23582 discloses conversion of hydantoins by an *Escherichia coli* that has been equipped with genetic material encoding the three enzymes hydantoinase, carbamoylase and hydantoin racemase of *Arthrobacter aurescens*, into enantiomerically pure α-amino acids.

Unfortunately, not all 5-substituted hydantoins are equally well accessible, whereas many of those would be highly desirable as chemical building blocks.

For instance, hydantoins [1] wherein $R_1$ is O-acyl or S-acyl or other O- or S-based leaving groups, form a class of compounds that has not been described, with only one exception, i.e. S-acetylcysteine hydantoin as described by Oh et al. (Archiv der Pharmazie, 328(4), 385-7 (1995)). Likewise, hydantoins [1] wherein $R_1$ is a cyclic alkene, for instance a cyclic enamine, or cyclic keto-alkane group are also unknown. However, this specific class of compounds would be a suitable candidate for the multi-enzyme mediated synthesis of enantiomerically pure α-amino acids as outlined above as the resulting α-amino acids can be used as building blocks for several active pharmaceutical ingredients.

Hence, there is a need for the 5-substituted hydantoins as described above, methods for their preparation and use of these 5-substituted hydantoins in the synthesis of active pharmaceutical ingredients.

DETAILED DESCRIPTION OF THE INVENTION

In the first aspect of the present invention, a new class of 5-substituted hydantoins is provided, namely compounds of the general formula [1]

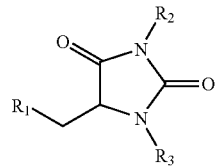

[1]

wherein $R_1$ is —Z—$R_{11}$ with Z is O or S or S(O) or S(O)$_2$ and $R_{11}$ is —C(O)$R_{111}$ or —S(O)$R_{111}$ or —S(O)$_2R_{111}$; or wherein $R_1$ is

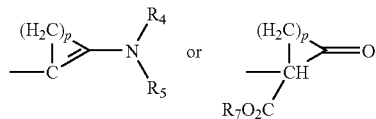

and wherein p has the value 1, 2, 3, 4, 5 or 6 and wherein $R_4$ and $R_5$ are independently chosen from the list consisting of —CH$_3$, —CH$_2$CH$_3$, —CH$_2$CH$_2$CH$_3$, —C$_6$H$_6$, lower alkyl, aryl or wherein $R_4$ and $R_5$ are connected to each other to form a ring chosen from the list consisting of —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$ACH$_2$— wherein A is —(CH$_2$)$_q$S—, —(CH$_2$)$_q$S—, —(CH$_2$)$_q$S(O)—, —(CH$_2$)$_q$S(O)$_2$— with q is 0, 1, 2, 3 or 4 and $R_2$ is —H or —C(O)$R_{22}$ or —S(O)$R_{22}$ or —S(O)$_2R_{22}$ and $R_3$ is —H or —C(O)$R_{33}$ or —S(O)$R_{33}$ or —S(O)$_2R_{33}$, wherein $R_{111}$, $R_{22}$ and $R_{33}$ are independently chosen from the list consisting of —H, —CH$_3$, —CH$_2$X, —CHX$_2$, —CX$_3$, —C$_6$H$_6$, —C$_6$H$_5$X, —C$_6$H$_4$X$_2$, lower alkyl and aryl, wherein X represents Br, CH$_3$, C$_2$H$_5$, NO$_2$, Cl, F or I, with the proviso that $R_2$ and $R_3$ are not —H when Z is S and $R_{11}$ is —C(O)CH$_3$ and wherein $R_7$ is chosen from the list consisting of —CH$_3$, —CH$_2$CH$_3$, —CH$_2$CH$_2$CH$_3$, —C$_6$H$_6$, lower alkyl, aryl and substituted derivatives thereof. The term lower alkyl is meant to encompass all linear and branched, saturated and (partially) unsaturated, hydrocarbons with up to 10 carbon atoms, such as for instance methyl, ethyl, propyl, iso-propyl, butyl, iso-butyl, sec-butyl.

Of the compounds mentioned above, preferably at least $R_1$ is a leaving group such as O-acetyl, O-mesyl, O-formyl, O-tosyl, O-tribromoacetyl, O-trichloroacetyl, O-trifluoroacetyl, S-acetyl, S-mesyl, S-formyl, S-tosyl, S-tribromoacetyl, S-trichloroacetyl S-trifluoroacetyl and the like. $R_2$ is preferably hydrogen or the same as $R_{11}$ and the same applies to $R_3$. Still more preferred compounds are compounds of formula [1] wherein $R_1$ is —Z—$R_{11}$ with Z is O or S and $R_{11}$ is —C(O)H or —C(O)CH$_3$ and $R_2$ and $R_3$ are both —H or both the same as $R_{11}$. Alternatively, of the compounds mentioned above, preferably $R_1$ is a cyclic alkene or cyclic keto-alkane as this specific class of compounds can be used as substrate for multi-enzyme mediated synthesis of enantiomerically pure α-amino acids.

The compounds of the first aspect of the invention include the racemic forms as well as the optically pure forms as well as mixtures of the two forms. When starting from cheap naturally occurring L-amino acids, the S-enantiomers of compounds [1] are thus predominantly formed and included in the present invention.

In the second aspect of the present invention, a method for the preparation of the compounds of the first aspect is provided. It has been found that the 5-substituted hydantoins of the present invention can be successfully prepared starting from easily accessible compounds such as amino acid hydantoins of formula [2]

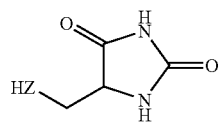

[2]

wherein Z is O (serine hydantoin, prepared for instance from L-serine according to Pham et al. (J. Org. Chem. 70, 6369-6377 (2005)) or S (cysteine hydantoin, prepared for instance from L-cysteine according to Oh et al. (Archiv der Pharmazie, 328(4), 385-7 (1995)) by contacting said compounds [2] with a suitable agent.

In a first embodiment, compound [2] is contacted with an acylating agent of formula $R_{111}C(O)_Y$ wherein $R_{111}$ is chosen from the list consisting of —H, —$CH_3$, —$CH_2X$, —$CHX_2$, —$CX_3$, —$C_6H_6$, —$C_6H_5X$, —$C_6H_4X_2$, tert-butyl, lower alkyl and aryl, wherein X represents Br, $CH_3$, $C_2H_5$, $NO_2$, Cl, F or I and wherein Y represents Br, Cl, F, I, OH or OC(O)$R_{1111}$. $R_{1111}$ will in most cases be the same as $R_{111}$, however also compounds wherein $R_{1111}$ differs from $R_{111}$ are included in the present invention. Hence, $R_{1111}$ may be independently chosen from the list consisting of —$CH_3$, —$CH_2X$, —$CHX_2$, —$CX_3$, —$C_6H_6$, —$C_6H_5X$, —$C_6H_4X_2$, tert-butyl, lower alkyl and aryl with X having the meaning outlined above. Particularly suitable acylating agents are acetyl chloride, preferably in the presence of an organic base such as pyridine, 4-dimethylamino pyridine, lutidine (such as 3,5-lutidine), imidazole or triethylamine, acetic anhydride and an organic base as above, formic acid in the presence of an anhydride such as acetic anhydride and the like. The molar amounts of acylating agent and base should be the same, preferably with an error margin not exceeding 25%, more preferably not exceeding 10%, still more preferably not exceeding 5%, most preferably within 0.1 to 2%. The amount of acylating agent and base with respect to compound [2] should be equimolar, twice equimolar or three times equimolar, depending on the number of substitutions one desires to make. Preferably the amount of acylating agent and base with respect to compound [2] is slightly higher than equimolar, twice equimolar or three times equimolar. The term 'slightly' in this respect is to be interpreted as up to 25%, preferably up to 15%, more preferably up to 5%, most preferably up to 2%. Suitable solvents are inert solvents such as alkylnitriles, esters, ethers, (halogenated) hydrocarbons and the like. Preferred solvents are acetonitrile and dichloromethane. The skilled person will understand that the reaction temperature may vary widely, depending on the nature of the substrates. Preferred temperatures are from −30 to 50° C., more preferably from −10 to 30° C., most preferably from −5 to 15° C.

In a second embodiment, compound [2] is contacted with a sulfonylating agent of formula $R_{111}S(O)_nY$ wherein n is 1 or 2 and $R_{111}$ is chosen from the list consisting of —$CH_3$, —$CH_2X$, —$CHX_2$, —$CX_3$, —$C_6H_6$, —$C_6H_5X$, —$C_6H_4X_2$, tert-butyl, lower alkyl and aryl, wherein X represents Br, $CH_3$, $C_2H_5$, $NO_2$, Cl, F or I and wherein Y represents Br, Cl, F, I, OH or $OS(O)_nR_{1111}$. $R_{1111}$ will in most cases be the same as $R_{111}$, however also compounds wherein $R_{1111}$ differs from $R_{111}$ are included in the present invention. Hence, $R_{1111}$ may be independently chosen from the list consisting of —$CH_3$, —$CH_2X$, —$CHX_2$, —$CX_3$, —$C_6H_6$, —$C_6H_5X$, —$C_6H_4X_2$, tert-butyl, lower alkyl and aryl with X having the meaning outlined above. Particularly suitable agents are p-toluenesulfonyl chloride (tosyl chloride), 2-, 3- or 4-nitrobenzenesulfonyl chloride (nosyl chloride), methanesulfonyl chloride (mesyl chloride) and trifluoromethanesulfonyl chloride, preferably in the presence of an organic base such as pyridine, 4-dimethylamino pyridine, lutidine, imidazole or triethylamine. The molar amounts of sulfonylating agent and base should be the same, preferably with an error margin not exceeding 25%, more preferably not exceeding 10%, still more preferably not exceeding 5%, most preferably within 0.1 to 2%. The amount of sulfonylating agent and base with respect to compound [2] should be equimolar, twice equimolar or three times equimolar, depending on the number of substitutions one desires to make. Preferably the amount of acylating agent and base with respect to compound [2] is slightly higher than equimolar, twice equimolar or three times equimolar. The term 'slightly' in this respect is to be interpreted as up to 25%, preferably up to 15%, more preferably up to 5%, most preferably up to 2%.

In a third embodiment, the methods as described in the first and second embodiments are further expanded by the addition to said compounds of general formula [1] of an enamine of general formula [3], followed by enamine hydrolysis or with a ketoester of general formula [3a]

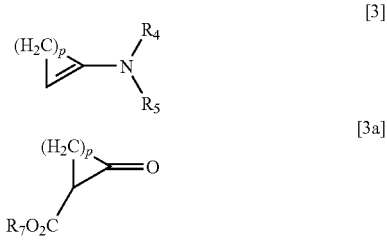

wherein p has the value 1, 2, 3, 4, 5 or 6 and wherein $R_4$ and $R_5$ are independently chosen from the list consisting of —$CH_3$, —$CH_2CH_3$, —$CH_2CH_2CH_3$, —$C_6H_6$, lower alkyl, aryl or wherein $R_4$ and $R_5$ are connected to each other to form a ring chosen from the list consisting of —$CH_2CH_2$—, —$CH_2CH_2CH_2$—, —$CH_2CH_2CH_2CH_2$—, —$CH_2CH_2CH_2CH_2CH_2$— and —$CH_2ACH_2$— wherein A is —$(CH_2)_qO$—, —$(CH_2)_qS$—, —$(CH_2)_gS(O)$—, —$(CH_2)_gS(O)_2$— with q is 0, 1, 2, 3 or 4, and wherein $R_7$ is chosen from the list consisting of —$CH_3$, —$CH_2CH_3$, —$CH_2CH_2CH_3$, —$C_6H_6$, lower alkyl, aryl and substituted derivatives thereof to give a compound of the general formula [4] after hydrolysis

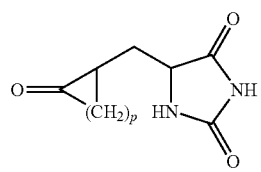

[4]

Formation of [4] requires a hydrolysis step. Preferably the method of the third embodiment is carried out in the presence of a base, preferably an organic base. Suitable examples are 1,8-diazabicyclo[5.4.0]undec-7-ene, N,N-diethylmethylamine, N,N-diisopropylethylamine N,N-dimethylethylamine, N-methylmorpholine, N-methylpiperidine, N,N,N',N'-tetramethylethylenediamine and triethylamine, preferably N,N-dimethylethylamine and N,N,N',N'-tetramethylethylenediamine. In case [3a] is added in the above described reaction, the most preferred bases are 1,8-diazabicyclo[5.4.0]undec-7-ene and the like. Suitable solvents are inert solvents such as alkylnitriles, esters, ethers, (halogenated) hydrocarbons and the like. Preferred solvents are acetonitrile and tetrahydrofuran and solvents that are also used in the first and second embodiments. Preferred temperatures are from −20 to 60° C., more preferably from 0 to 40° C., most preferably from 10 to 30° C. The formation of compounds [4, $R_7$=H] usually occurs through intermediacy of compounds of formula [1] wherein $R_2$ and $R_3$ are defined as above and $R_1$ is a fragment of the general structure [3b].

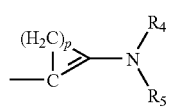

[3b]

wherein p, $R_4$ and $R_5$ are defined as above. Said compounds [1] can be isolated, purified if one so desires and are hitherto unknown compounds.

In a fourth embodiment, the method as described in the third embodiment is further expanded by bioconversion of said compound of general formula [4] to give a compound of general formula [5]

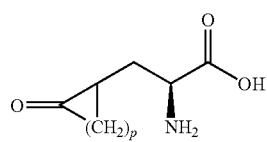

[5]

wherein p has the value 1, 2, 3, 4, 5 or 6, which has the S-configuration at the nitrogen-substituted carbon atom, preferably with an ee-value>95%, more preferably >98%, most preferably >99.5%. The preferred values of p are 3 and 4 as products [5] having these values can serve as optically pure intermediates for the angiotensin-converting enzyme (ACE) inhibitors ramipril and perindopril, respectively.

Preferably, said bioconversion is carried out by the action of the enzymes hydantoinase, carbamoylase and hydantoin racemase. These enzymes may be used in vitro or in vivo. In the latter case it is advantageous to incorporate the genetic information for all three enzymes in a single organism, i.e. as in WO 2001/23582. Suitably the three genes encoding the respective enzymes hydantoinase, carbamoylase and hydantoin racemase are under the control of a single promoter. Promoters useful according to the present invention are promoters suited for expression of genes in the particular recombinant micro-organism. Examples of such promoters are inducible promoters for operons/genes like the lactose operon (lac), the rhamnose operon (rha), the arabinose operon (ara), the tryptophan operon (trp), the operon encoding enzymes common to the biosynthesis of all aromatic amino acids (aro), or functional hybrids of these. Other examples of useful promoters are constitutive promoters. The DNA sequences encoding the respective enzymes may be the sequences occurring naturally, or may be synthetic sequences. The synthetic sequences may be adapted compared to the naturally occurring sequences e.g. by using codons for the amino acids which are more suitable for expression in the particular recombinant microorganism selected for the whole cell catalytic systems of the present invention. Suitable microorganisms for use according to the invention are prokaryotes and in particular bacteria, and more in particular *Escherichia coli*.

In a fifth embodiment, the method as described in the fourth embodiment is further expanded by subjecting said compound of general formula [5] to hydrogenation to give a compound of general formula [6]

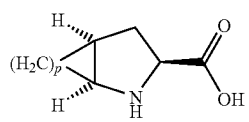

[6]

wherein p has the value 1, 2, 3, 4, 5 or 6 which predominantly has the S,S,S-configuration, preferably >85%, more preferably >90%, most preferably >95%. The preferred values of p are 3 and 4 as products [6] having these values can serve as intermediates for the ACE inhibitors ramipril and perindopril, respectively.

Preferably, hydrogenation is carried out in the presence of a suitable metal-based heterogeneous catalyst or a metal-based homogeneous catalyst. Metal-based heterogeneous catalysts can be, for instance, palladium on carbon or platinum on carbon. Metal-based homogeneous catalysts can be based on, for instance, ruthenium, rhodium, iridium, and the like, with or without ligand. Hydrogenation can be carried out in a suitable polar solvent such as water, methanol, ethanol, acetic acid or mixtures thereof, under a pressure of hydrogen gas between 1 and 10 bar, preferably 1 to 5 bar, most preferably 5 bar, at a temperature between 0 and 60° C., preferably between 10 and 30° C., most preferably between 15 and 25° C.

In a sixth embodiment, the method as described in the fifth embodiment is further expanded by reacting said compound of general formula [6] with a carboxylic acid or with an activated carboxylic acid, preferably with an "activated" form of a compound of general formula [7] or with a compound of general formula [8]

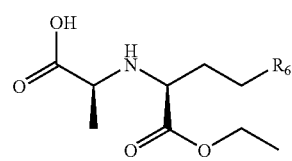

[7]

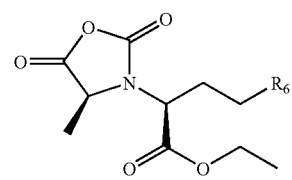

[8]

wherein $R_6$ is alkyl or aryl, preferably —$CH_3$ or phenyl, to give a compound of formula [9]

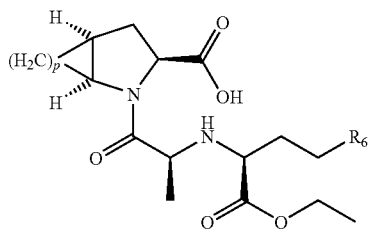

wherein p has the value 1, 2, 3, 4, 5 or 6. Preferably p has the value 3 and $R_6$ is phenyl (ramipril) or p has the value 4 and $R_6$ is —$CH_3$ (perindopril). Optionally, the carboxylic acid group of compound [6] is protected prior to reaction with compound [7] or its activated form or [8] with the objective to circumvent unwanted side-reactions. The person skilled in the art is aware of the various protecting groups suitable for this purpose. Particularly suitable is protection of compound [6] as a benzyl ester or as a substituted benzyl ester. After reaction with compound [7] or [8], the resulting carboxylic acid protected derivative of compound [9] can be deprotected to furnish compound [9] using standard techniques. When the protecting group is a benzyl ester or as a substituted benzyl ester, deprotection can for instance be carried out using hydrogenation.

EXAMPLES

Example 1

Preparation of tris-acetyl 5-hydroxymethylimidazolidine-2,4-dione ([1], $R_1$=—OC(O)$CH_3$, $R_2$=$R_3$=—C(O)$CH_3$)

L-Serine hydantoin (41.4 g, 318 mmol) was suspended in dry MeCN (330 mL) and the solution was cooled to 10° C. Pyridine (88.3 g, 1.11 mol) was added followed by drop wise addition during approx. 1 h of acetyl chloride (87.4 g, 1.11 mol), such that the temperature was maintained at 10° C. After the addition, the reaction was allowed to warm up to 20° C. while a precipitate formed that gradually dissolved. After approx. 16 h, the reaction was complete (as determined by $^1$H NMR in $CDCl_3$) and was concentrated on the rotavapor at 40° C. to a weight of approx. 240 g during which some solids formed. MTBE (500 mL) was added and more solid precipitated. After stirring for 10 min, the precipitate was collected on a funnel via suction. The cake was washed with additional MTBE (100 mL) and then discarded. The title product resided in the mother liquor. This was concentrated on a rotavapor at 40° C. to thick oil. Weight 73.0 g, ca. 95% purity, approx. 85% yield. $^1$H NMR: ($CDCl_3$, 300 MHz): δ 4.83 (dd, 1H), 4.73 (t, 1H), 4.44 (dd, 1H), 2.61 (s, 3H), 2.60 (s, 3H), 2.03 (s, 3H).

Example 2

Preparation of O-formyl 5-hydroxymethylimidazolidine-2,4-dione ([1], $R_1$=—OC(O)H, $R_2$=$R_3$=—H)

L-Serine hydantoin (20.0 g, 154 mmol) was suspended in formic acid (100 mL) and acetic anhydride (50 mL, 530 mmol) was dosed into the reaction mixture during a period of 1 h at 10±3° C. Afterwards, the heterogeneous mixture was allowed to reach room temperature. Within approx. 2 h, the reaction mixture was clear and colorless and the conversion was complete according to HPLC analysis. Formic acid and acetic acid were removed under reduced pressure at 40±3° C. affording colorless and viscous oil that was subsequently dosed into MTBE (200 mL). A slurry formed which was stirred for 12 h. White crystalline material was isolated by filtration through a frit (porosity 3) under suction to give 16.6 g (70% yield) of the title product. $^1$H NMR: (DMSO-$d_6$, 300 MHz): δ 10.7 (br s, 1H), 8.27 (s, 1H), 8.00 (s, 1H), 4.33-4.37 (q, 1H), 4.15-4.26 (m, 1H).

Example 3

Preparation of tris-acetyl 5-thiomethylimidazolidine-2,4-dione ([1], $R_1$=—SC(O)$CH_3$, $R_2$=$R_3$=—C(O)$CH_3$)

L-Cysteine hydantoin (8.00 g, 54.7 mmol) was suspended in dry MeCN (100 mL) and the solution was cooled to 10° C. Pyridine (15.2 g, 192 mmol) was added followed by drop wise addition during approx. 1 h of acetyl chloride (15.0 g, 192 mmol), such that the temperature was maintained at 10° C. After the addition, the reaction was allowed to warm up to 20° C. while a precipitate formed that gradually dissolved. After approx. 16 h, the reaction was complete (as determined by $^1$H NMR in $CDCl_3$) and was concentrated on the rotavapor at 40° C. to thick oil. Some solids formed. MTBE (67 mL) was added and more solid precipitated. After stirring for 10 min, the precipitate was collected on a funnel via suction. The cake was washed with additional MTBE (3×25 mL) and then discarded. The title compound resided in the mother liquor which was concentrated on a rotavapor at 40° C. to thick oil. Weight 14.5 g, approx. 95% purity, approx. 92% yield. $^1$H NMR: ($CDCl_3$, 300 MHz): δ 4.86 (dd, 1H), 3.87 (dd, 1H), 3.40 (dd, 1H), 2.59 (s, 3H), 2.56 (s, 3H), 2.34 (s, 3H).

Example 4

Preparation of S-trichloroacetyl 5-thiomethylimidazolidine-2,4-dione ([1], $R_1$=—SC(O)$CCl_3$, $R_2$=$R_3$=—H)

L-Cysteine hydantoin (5.00 g, 34.2 mmol) was suspended in dry MeCN (60 mL) and the solution was cooled to 0° C. Pyridine (2.98 g, 37.2 mmol) was added followed by drop wise addition during approx. 10 min of trichloroacetic anhydride (11.6 g, 37.6 mmol dissolved in 20 mL of dry MeCN), such that the temperature was maintained at <5° C. After the addition, the reaction was allowed to warm up to 20° C. while a precipitate formed. After 3 h, the reaction was complete (as determined by $^1$H NMR in $CD_3CN$). The product was collected by filtration under suction (filter porosity 3). Weight 6.00 g, >95% purity, approx. 60% yield. $^1$H NMR: ($CDCl_3$+drop DMSO-$d_6$, 300 MHz): δ 10.16 (br s, 1H), 6.97 (br s, 1H), 4.29 (dt, 1H), 3.46 (AB, 2H).

Example 5

Preparation of O-trichloroacetyl 5-hydroxymethylimidazolidine-2,4-dione ([1], $R_1$=—OC(O)$CCl_3$, $R_2$=$R_3$=—H)

L-Serine hydantoin (5.00 g, 38.4 mmol) was suspended in dry MeCN (60 mL) and cooled to 0° C. Pyridine (3.34 g, 42.3 mmol) was added and a homogeneous solution formed. Trichloroacetic anhydride (13.0 g, 42.3 mmol) in dry MeCN (20 mL) was added drop wise during approximately 10 min, so that the temperature was maintained <5° C. After completion of the addition, the reaction was allowed to warm up to 20° C. (within approx. 30 min). A small amount of precipitate formed. After 3 h, the reaction was complete (as determined by $^1$H NMR in CDCl$_3$). The solution was concentrated on a rotavapor at 40° C. to thick oil which solidified upon standing within minutes. The residue was resuspended in water (50 mL) and stirred for 10 min to dissolve the salt (reaction by-product). The product was collected by filtration under suction (filter porosity 3). Off-white solid. Weight 7.72 g, >95% purity, approx. 73% yield. $^1$H NMR: (DMSO-d$_6$, 300 MHz): δ 10.84 (br s, 1H), 8.04 (br s, 1H), 4.61 (AB, 2H), 4.50-4.48 (m, 1H).

Example 6

Preparation of O-dichloroacetyl 5-hydroxymethylimidazolidine-2,4-dione ([1], $R_1$=—OC(O)CHCl$_2$, $R_2$=$R_3$=—H)

L-Serine hydantoin (5.00 g, 38.4 mmol) was suspended in dry MeCN (60 mL) and the solution was cooled to 0° C. Pyridine (3.34 g, 42.3 mmol) was then added and a homogeneous solution formed. Dichloroacetyl chloride (6.23 g, 42.3 mmol) was added as a solution in dry MeCN (20 mL) via addition funnel drop wise during approx. 10 min, so that the reaction temperature was maintained <5° C. After completion of the addition, the reaction was allowed to warm up to 20° C. (within approx. 30 min). A small amount of precipitate formed. After 14 h, the mixture was concentrated on a rotavapor at 40° C. The residue was resuspended in water (15 mL) and the product was extracted into MTBE (3×30 mL). The combined organic layers were dried over anhydrous Na$_2$SO$_4$. After filtration and evaporation of the solvent in vacuo at 50° C., the product was obtained as a yellowish solid which was resuspended and stirred for 15 min in diethyl ether (20 mL) and then collected by filtration under suction (filter porosity 3). Off-white solid. Weight 8.33 g, >95% purity, approx. 90% yield. $^1$H NMR: (DMSO-d$_6$, 300 MHz): δ 10.80 (br s, 1H), 8.00 (br s, 1H), 6.92 (s, 1H), 4.54-4.39 (m, 3H).

Example 7

Preparation of 5-((2-(pyrrolidin-1-yl)cyclopent-1-enyl)methyl)imidazolidine-2,4-dione ([1], $R_1$=$R_2$=$R_3$=—H) from O-formyl 5-hydroxymethylimidazolidine-2,4-dione

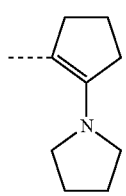

O-formyl 5-hydroxymethylimidazolidine-2,4-dione obtained in Example 2 (2.00 g, 12.6 mmol) was suspended in THF (20 mL) with stirring at room temperature. In a separate flask, triethylamine (1.28 g, 12.6 mmol) and 1-pyrrolidino-1-cyclopentene (1.73 g, 12.6 mmol) are mixed and subsequently dosed into the THF suspension during a period of approx. 1 h. After 3 days the conversion was complete (HPLC). The heterogeneous mixture was filtered off under suction on a fritted funnel and the solid product was washed with THF (5 mL) and was allowed to dry in the air. Weight: 1.10 g, 35% yield. $^1$H NMR: (CD$_3$CN, 300 MHz): δ 8.25 (br s, 1H), 4.31 (dd, 1H), 3.04 (q, 1H), 2.77-2.69 (m, 4H), 2.37 (ddd, 1H), 1.84-1.40 (m, 10H).

Example 8

Preparation of 5-((2-oxocyclopentyl)methyl)imidazolidine-2,4-dione ([4], p=3) from tris-acetyl 5-hydroxymethylimidazolidine-2,4-dione Tris-acetyl 5-hydroxymethylimidazolidine-2,4-dione obtained in Example 1 (6.06 g, 95% pure, 22.5 mmol) was dissolved in THF (25 mL) and added drop wise into a solution of triethylamine (3.57 g, 35.3 mmol) and 1-pyrrolidino-1-cyclopentene (4.85 g, 35.3 mmol) in THF (25 mL) at 20° C. over a period of approx. 45 min. The homogeneous, yellow-orange reaction was stirred further for 16 h at 20° C. The conversion was complete as determined by $^1$H NMR in DMSO-d$_6$. Water (8 mL) was added followed by conc. aq. HCl (3 mL). After stirring for 30 min, the solvent was removed on the rotavapor at 40° C. Water (15 mL) was added and the product was extracted into EtOAc (2×25 mL) and the combined organic extracts were dried over anhydrous Na$_2$SO$_4$. After filtration and concentration of the solution on the rotavapor at 60° C., the product, N$_4$-acetyl-[4] was purified by silica gel flash chromatography using an EtOAc:petroleum benzene gradient. Weight 4.35 g, 81% yield. The product N$_3$-acetyl-[4] is a ca. 1:1 mixture of diastereomers. $^1$H NMR: (CDCl$_3$, 300 MHz): δ 8.49 (br s, 1H), 4.82 (dd, 0.5H), 4.63 (dd, 0.5H), 2.57 (s, 3H), 2.46-2.00 (m, 7H), 1.88-1.75 (m, 1H), 1.67-1.53 (m, 1H). N$_3$-acetyl-[4] (0.500 g, 2.10 mmol) was dissolved in 6M aq. HCl and was stirred at 80° C. for 16 h. The conversion was followed by TLC on silica-coated plates (eluent 7:3 EtOAc:petroleum benzene). The reaction mixture was cooled to 20° C. and extracted with ethyl ether (10 mL). The aqueous phase was separated and concentrated on the rotavapor at 70° C. to give title compound [4] (mixture of diastereomers) as a brownish solid. Weight 0.360 g, 87% yield. $^1$H NMR: (DMSO-d$_6$, 300 MHz): δ 10.63 (br s, 1H), 7.99 (br s, 0.73H, major diastereomer), 7.90 (br s, 0.27H, minor diastereomer), 4.19 (td, 0.27H, minor diastereomer), 4.06 (ddd, 0.73H, major diastereomer), 2.30-2.02 (m, 4H), 1.98-1.80, 2H), 1.77-1.62 (m, 1H), 1.60-1.40 (m, 2H).

Example 9

Preparation of 5-((2-oxocyclopentyl)methyl)imidazolidine-2,4-dione ([4], p=3) from O-formyl 5-hydroxymethylimidazolidine-2,4-dione O-formyl 5-hydroxymethylimidazolidine-2,4-dione obtained in Example 2 (2.00 g, 12.6 mmol) was suspended in THF (20 mL) with stirring at room temperature. In a separate flask, triethylamine (1.28 g, 12.6 mmol) and 1-pyrrolidino-1-cyclopentene (1.73 g, 12.6 mmol) are mixed and subsequently dosed into the THF suspension during a period of approx. 1 h. After 3 days the conversion was complete (HPLC). Then, water (2 mL) was added and the pH was adjusted to 0 with 37% HCl (approx. 2.5 mL). The product was extracted into iso-PrOAc (1×20 mL and 2×10 mL) and the combined organic extracts were concentrated under reduced pressure affording the title compound as a colorless solid. Weight 1.36 g, 55% yield. $^1$H NMR: (DMSO-d$_6$, 300 MHz): δ 10.6 (br s, 1H), 7.90 (br s, 1H), 4.04-4.19 (m, 1H), 1.57-2.26 (m, 2H), 1.57-2.26 (m, 7H).

Example 10

Preparation of 5-((2-oxocyclopentyl)methyl)imidazolidine-2,4-dione ([4], p=3) from tris-acetyl 5-thiomethylimidazolidine-2,4-dione Tris-acetyl 5-thiomethylimidazolidine-2,4-dione obtained in Example 3 (5.00 g, 95% pure, 17.4 mmol) was dissolved in MeCN (20 mL) and added drop wise via an addition funnel into a solution of triethylamine (2.79 g, 27.6 mmol) and 1-pyrrolidino-1-cyclopentene (3.78 g, 27.6 mmol) in MeCN (20 mL) at 20° C. over a period of 45 min. The homogeneous, yellow-orange reaction was stirred for 16 h at 20° C. The conversion was complete as determined by $^1$H NMR in DMSO-$d_6$. Then, 6N aq. HCl (10 mL) was added. After stirring for 30 min, the solvent was removed on the rotavapor at 40° C. The product was extracted into EtOAc (3×40 mL) and the combined organic extracts were dried over anhydrous $Na_2SO_4$. After filtration and concentration of the solution on the rotavapor at 60° C., the product $N_4$-acetyl-[4] was purified by silica gel flash chromatography using an EtOAc:petroleum benzene gradient. Weight 3.10 g, 75% yield. The product $N_3$-acetyl-[4] has the same characteristics as described under Example 8 and was deacetylated as described under Example 8 to give the title compound.

Example 11

Preparation of 5-((2-oxocyclohexyl)methyl)imidazolidine-2,4-dione ([4], p=4) from tris-acetyl 5-hydroxymethylimidazolidine-2,4-dione Tris-acetyl 5-hydroxymethylimidazolidine-2,4-dione obtained in Example 1 (17.0 g, 95% pure, 63 mmol) was dissolved in THF (110 mL) in an addition funnel and in a separate addition funnel, triethylamine (6.7 g, 66 mmol) was dissolved in THF (110 mL). These solutions were added simultaneously dropwise into a solution of 1-pyrrolidino-1-cyclohexene (14.9 g, 98 mmol) in THF (85 mL) at 20° C. over a period of approx. 1.5 h. The homogeneous, yellow-orange reaction was stirred further for 2 h at 20° C. The conversion was complete as determined by $^1$H NMR in DMSO-$d_6$. Then, the reaction was concentrated in vacuo and then aq. 6M HCl (30 mL, 180 mmol) was added to the residue and the product was extracted into i-PrOAc (3×75 mL). The combined organic phases were dried over anhydrous $Na_2SO_4$. After filtration and concentration of the solution at 60° C., the product, 1-acetyl-5-((2-oxocyclohexyl)methyl)imidazolidine-2,4-dione (a 3:2 mixture of diastereomers as judged by $^1$H NMR in $CDCl_3$), was isolated as a brown oil. Weight 15.0 g, 90% yield. The product (15.0 g, 59.5 mmol) was dissolved in water (66 mL) and concentrated aqueous HCl (7 mL) was added to pH=0 and the mixture was stirred at 80° C. for 16 h. The conversion was followed by TLC on silica-coated plates. The reaction mixture was then cooled to 20° C. and when some solid appeared, ethyl ether (60 mL) was added with vigorous stirring, causing precipitation of more product. After 30 min, the colorless solid was collected on a filter under suction, washed with some ethyl ether and allowed to air-dry. The title product thus obtained is a 2:3 mixture of diastereomers. Weight 4.41 g, 35% yield. $^1$H NMR: (DMSO-$d_6$, 300 MHz): δ 10.50 (br s, 1H), 7.85 (br s, 0.42H, minor diastereomer), 7.76 (br s, 0.58H, major diastereomer), 3.97-3.89 (m, 1H), 2.57-2.47 (m, 1H), 2.33-2.21 (m, 1H), 2.17-1.74 (m, 4H), 1.70-1.05 (m, 5H).

Example 12

Preparation of (S)-2-amino-3-(2-oxocyclopentyl) propanoic acid ([5], p=3) from 5-((2-oxocyclopentyl)methyl)imidazolidine-2,4-dione ([4], p=3)

Protocol for Transformation of pKECaroP-hyu1 Construct into *Escherichia coli* RV308
Thaw *Escherichia coli* RV308 aliquots (200 μl, super competent) on ice
Add 15 μl LR reaction mix (see above)
Incubate 30 minutes on ice
Heat shock 1 minute 42° C.
Cool cells 2 minutes on ice
Add 1 ml LB medium (5 g/l NaCl, 5 g/l yeast extract, 10 g/l tryptone)
Incubate 1 hour 37° C.
Plate on LB agar plates supplemented with kanamycine (5 g/l NaCl, 5 g/l yeast extract, 10 g/l tryptone, 15 g/l agar, 50 mg/l kanamycine)
Incubate 24 hours 28° C.
Isolate single colonies
Protocol for Expression of Hyu Genes in *Escherichia coli* RV308
Single clones from the transformation (see above) were used to inoculate 5 ml of 2×TY media (10 g/l yeast extract, 16 g/l tryptone, 5 g/l NaCl) supplemented with 0.05 g/l kanamycine and 1 mM $MnCl_2$ or $CoCl_2$, respectively. The culture was incubated at 28° C. and 150 rpm for 24 hours and then used for inoculation of 100 ml 2×TY media supplemented with 0.05 g/l kanamycine and 1 mM $MnCl_2$ or $CoCl_2$, respectively. The cultures were again incubated for 24-28 hours under conditions previously mentioned and subsequently harvested by centrifugation (20 minutes, 5000 rpm, 4° C.). The cell pellet was resuspended in 5 ml Tris-HCl (100 mM, pH 7), centrifuged again (20 minutes, 5000 rpm, 4° C.) and the cells were frozen at ±20° C.
Bioconversion
5-((2-oxocyclopentyl)methyl)imidazolidine-2,4-dione ([4], p=3, 0.20 g, 1.0 mmol) was suspended in TRIS-HCl buffer (400 mM, 5 mL) at pH 8.5. Then, 0.8 g of wet cell slurry obtained according to 'Protocol for expression of Hyu genes in *Escherichia coli* RV308' was added, followed by 50 μL of a 100 mmol/L $MnCl_2$ solution and the mixture was incubated overnight at 37° C. The mixture was then centrifuged at room temperature and the supernatant was filtered through a 0.45 μl a filter. The product amino acid ([5], p=3) has the S configuration at C2 with >99% ee (the other chiral center C4 is scrambled). The diastereomeric product mixture was further purified by ion exchange column chromatography using acidic DOWEX 50WX2-100 (0.6 meq/mL) resin. Evaporation of the aqueous eluent in vacuo at 80° C. provided the product mixture as an off-brown solid. Weight 137 mg. 80% yield. $^1$H NMR: ($D_2O$, 300 MHz): δ 3.88-3.67 (m, 1H), 2.38-1.48 (m, 9H).

Example 12a

Preparation of (S)-2-amino-3-(2-oxocyclopentyl) propanoic acid ([5], p=3) from 5-((2-oxocyclopentyl)methyl)imidazolidine-2,4-dione ([4], p=3)

Example 12 was repeated, however the last part (bioconversion) was carried out as follows: 5-((2-oxocyclopentyl)methyl)imidazolidine-2,4-dione ([4], p=3, 0.20 g, 1.0 mmol) was suspended in water at pH 7.3. Then, 0.8 g of wet cell slurry obtained according to 'Protocol for expression of Hyu genes in *Escherichia coli* RV308' was added, followed by 50 µL of a 100 mmol/L $MnCl_2$ solution and the mixture was incubated overnight at 25-28° C. The biomass in the mixture was removed by filter press filtration and the supernatant was filtered through a 0.45µ a filter. The product amino acid ([5], p=3) has the S configuration at C2 with >99% ee (the other chiral center C4 is scrambled). Evaporation of the aqueous eluent in vacuo at 80° C. provided the product mixture as an off-brown solid. $^1$H NMR: ($D_2O$, 300 MHz): δ 3.88-3.67 (m, 1H), 2.38-1.48 (m, 9H).

Example 13

Preparation of (S)-2-amino-3-(2-oxocyclohexyl) propanoic acid ([5], p=4) from 5-((2-oxocyclohexyl) methyl)imidazolidine-2,4-dione ([4], p=4)

5-((2-oxocyclohexyl)methyl)imidazolidine-2,4-dione ([4], p=4, 1.0 mmol) was suspended in TRIS-HCl buffer (400 mM, 5 mL) at pH 8.5. Then, 0.8 g of wet cell slurry obtained according to 'Protocol for expression of Hyu genes in *Escherichia coli* RV308' in Example 10 was added, followed by 50 µL of a 100 mmol/L $MnCl_2$ solution and the mixture was incubated overnight at 37° C. The mixture was then centrifuged at room temperature and the supernatant was filtered through a 0.45µ filter. The product amino acid ([5], p=4) has the S configuration at C2 with >99% ee (the other chiral center C4 is scrambled) as determined by chiral HPLC.

Example 14

Preparation of (2S,3aS,6aS)-octahydrocyclopenta[b] pyrrole-2-carboxylic acid ([6], p=3) from (S)-2-amino-3-(2-oxocyclopentyl)propanoic acid ([5], p=3)

(S)-2-amino-3-(2-oxocyclopentyl)propanoic acid ([5], p=3, 130 mg, 0.76 mmol) was dissolved in water (2 mL) and the pH was adjusted to 9 with 25% aqueous $NH_3$ solution. Then, 10% Pd/C (5 mg) was added and hydrogenation was performed under 5 bar of hydrogen gas for 16 h. At the end of the reaction, the catalyst was filtered off on a pad of celite under suction and the product [6] was isolated after evaporation of the water layer in vacuo at 80° C. Weight 118 mg. 100% yield. Diastereomeric excess>95% (determined by chiral HPLC). $^1$H NMR: (DMSO-$d_6$, 300 MHz): δ 10.54 (br s, 1H), 8.71 (br s, 1H), 4.22 (dd, 1H), 3.98 (t, 1H), 2.86-2.76 (m, 1H), 2.49-2.42 (m, 1H), 2.00-1.96 (m, 1H), 1.80-1.40 (m, 6H).

Example 15

Preparation of (2S,3aS,6aS)-benzyl octahydrocyclopenta[b]pyrrole-2-carboxylate, 4-toluenesulfonate (1:1) from (2S,3aS,6aS)-octahydrocyclopenta[b] pyrrole-2-carboxylic acid ([6], p=3)

In a round-bottom flask equipped with a Dean-Stark trap, (2S,3aS,6aS)-octahydrocyclo-penta[b]pyrrole-2-carboxylic acid ([6], p=3, 5.00 g, 32.2 mmol) was suspended in toluene (100 mL) and p-toluenesulphonic acid monohydrate (6.60 g, 34.7 mmol) and benzyl alcohol (15.0 mL, 15.6 g, 144 mmol) were added and the mixture was brought to reflux. The reaction was refluxed for 8 h and then allowed to cool to room temperature. A colorless solid precipitated. Most of the solvent was then removed in vacuo at 65° C. To the residual thick suspension, ethyl ether (200 mL) was added and the solid was collected on a filter (porosity #3) under suction and was further washed with ethyl ether (4×50 mL). The colorless product was allowed to air-dry. Weight 12.1 g, 90% yield.

Example 16

Preparation of N—[(S)-1-(ethoxycarbonyl)-3-phenyl-propyl]-L-alanylchloride HCl from N—[(S)-1-(ethoxycarbonyl)-3-phenyl-propyl]-L-alanine N—[(S)-1-(ethoxycarbonyl)-3-phenyl-propyl]-L-alanylchloride HCl was synthesized from N-[(S)-1-(ethoxycarbonyl)-3-phenyl-propyl]-L-alanine ([7], $R_6$=phenyl) and $PCl_5$ in $CH_2Cl_2$ at 0±3° C. and precipitated by slow addition of cyclohexane as outlined in US 2006/0079698. Filtration was carried out under an atmosphere of nitrogen.

Example 17

Preparation of (2S,3aS,6aS)-octahydrocyclopenta[b] pyrrole-2-carboxylic acid, 1-[(2S)-2-[[(1S)-1-(ethoxycarbonyl)-3-phenylpropyl]amino]-1-oxopropyl], phenylmethyl ester from (2S,3aS,6aS)-benzyl octahydrocyclopenta[b]pyrrole-2-carboxylate The toluenesulfonate salt prepared in Example 15 (6.00 g, 14.4 mmol) was suspended in $CH_2Cl_2$ (60 mL) and triethylamine (1.46 g, 14.4 mmol) was added at 0° C. The slurry was stirred for 30 min and then imidazole (2.94 g, 43.1 mmol) was added in small portions, followed by N—[(S)-1-(ethoxycarbonyl)-3-phenyl-propyl]L-alanylchloride HCl prepared in Example 16 (5.28 g, 15.8 mmol). The reaction mixture was stirred for 2 h at 0° C. and then allowed to warm to 20° C. within 30 min and stirred at that temperature for 2 h. Water (60 mL) was then added and after vigorous mixing of the phases, the organic layer was separated and the aqueous layer was extracted once more with $CH_2Cl_2$ (60 mL). The combined organic layers were washed with aqueous saturated $NaHCO_3$ (60 mL), treated with charcoal (1 g) and dried over anhydrous $Na_2SO_4$ (5 g). After filtration of the salt and evaporation of the solvent in vacuo at 40° C., the product was obtained as a yellowish oil. This oil was redissolved in methanol (90 mL) and 5% Pd/C (0.50 g) was added and hydrogenation was performed under 2 bar of hydrogen pressure. After approx. 4 h, consumption of hydrogen ceased and the catalyst was filtered off on a pad of celite. Additional methanol was used to wash the celite (20 mL). The organic layer was removed in vacuo at 50° C. The residue was recrystallized from ethyl ether (100 mL) at 0° C. The product Ramipril ([9], p=3, $R_6$=phenyl) is a colorless solid. Weight 4.56 g, 70% yield.

Example 18

Preparation of 5-((2-oxocyclopentyl)methyl)imidazolidine-2,4-dione ([4], p=3) from tris-acetyl 5-hydroxymethylimidazolidine-2,4-dione Tris-acetyl 5-hydroxymethylimidazolidine-2,4-dione obtained in Example 1 (1.94 g, 95% pure, 7.2 mmol) was dissolved in toluene (10 mL) and ethyl 2-oxocyclopentanecarboxylate (1.19 g, 97%, 7.4 mmol) was added and the homogeneous, yellow-orange solution was cooled to 0° C. Then, DBU (1.72 g, 11.3 mmol) was added and the reaction was stirred for 1 h at 0° C. and then the cold bath was removed and the reaction was stirred for a further 1 h. The conversion was complete as determined by $^1$H NMR in $CDCl_3$. Then, 5% aq. citric acid solution (10 mL) was added to the reaction and after vigorous stirring, the organic phase was separated and the aqueous phase was extracted again with toluene (10 mL). The combined organic layers were dried over anhydrous $Na_2SO_4$. After filtration and evaporation of the solvent in vacuo, the product was purified by silica gel flash chromatography using an EtOAc:petroleum benzene gradient. When the fractions containing the product ethyl 1-((3-acetyl-2,5-dioxoimidazolidin-4-yl)methyl)-2-oxocyclopentanecarboxylate (mixture of diastereomers) were pooled and concentrated in vacuo to a volume of ca. 10 mL, and cooled to 20° C., a colorless solid appeared, which was filtered off under suction and washed with EtOAc:petroleum benzene and air-dried. Weight 820 mg, 37% yield. The product, ethyl 1-((3-acetyl-2,5-dioxoimidazolidin-4-yl)methyl)-2-oxocyclopentanecarboxylate, is a 1:1 mixture of diastereomers. $^1$H NMR: ($CDCl_3$, 300 MHz): δ 8.51-8.48 (br m, 1H), 4.74 (dd, 0.4H), 4.61 (dd, 0.6H), 4.18-4.07 (m, 2H), 2.83-2.56 (m, 2H), 2.52 (br m, 3H), 2.40-2.22 (m, 3H), 2.10-1.96 (m, 3H), 1.24 (t, 3H)

Ethyl 1-((3-acetyl-2,5-dioxoimidazolidin-4-yl)methyl)-2-oxocyclopentanecarboxylate (mixture of diastereomers) (700 mg, 2.25 mmol) was suspended in 1M aq. HCl (6.75 mL, 6.75 mmol) and the mixture was brought to a gentle reflux, during which time the substrate dissolved. The conversion was followed by $^1$H NMR in DMSO-$d_6$. The reaction was complete after a period of 15 h. Then the mixture was evaporated to dryness on the rotavapor at 70° C. to the title compound [4] (mixture of diastereomers) as a colorless solid, whose $^1$H NMR is the same as the one reported in Example 8. Weight: 432 mg, 98% yield.

The invention claimed is:

1. A compound of formula [1]

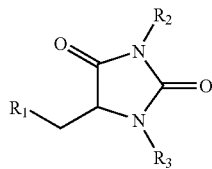

[1]

wherein $R_1$ is —Z—$R_{11}$ with Z is O or S or S(O) or $S(O)_2$ and $R_{11}$ is —C(O)$R_{111}$ or —S(O)$R_{111}$ or —S(O)$_2R_{111}$ or wherein $R_1$ is

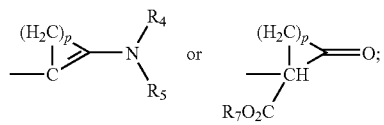

and wherein
p has the value 1, 2, 3, 4, 5 or 6 and wherein $R_4$ and $R_5$ are independently chosen from the list consisting of —$CH_3$, —$CH_2CH_3$, —$CH_2CH_2CH_3$, —$C_6H_6$, lower alkyl, aryl or wherein $R_4$ and $R_5$ are connected to each other to form a ring chosen from the list consisting of —$CH_2CH_2$—, —$CH_2CH_2CH_2$—, —$CH_2CH_2CH_2CH_2$—, —$CH_2CH_2CH_2CH_2CH_2$— and —$CH_2ACH_2$— wherein A is —$(CH_2)_qO$—, —$(CH_2)_qS$—, —$(CH_2)_qS(O)$—, —$(CH_2)_qS(O)_2$— with q is 0, 1, 2, 3 or 4; and
$R_2$ is —H or —C(O)$R_{22}$ or —S(O)$R_{22}$ or —S(O)$_2R_{22}$; and
$R_3$ is —H or —C(O)$R_{33}$ or —S(O)$R_{33}$ or —S(O)$_2R_{33}$; and wherein $R_{111}$, $R_{22}$ and $R_{33}$ are independently chosen from the list consisting of —H, —$CH_3$, —$CH_2X$, —$CHX_2$, —$CX_3$, —$C_6H_6$, —$C_6H_5X$, —$C_6H_4X_2$ lower alkyl and aryl, wherein X represents Br, $CH_3$, $C_2H_5$, Cl, F or I, with the proviso that $R_2$ and $R_3$ are not —H when Z is S and $R_{11}$ is —C(O)$CH_3$; and wherein
$R_7$ is chosen from the list consisting of —$CH_3$, —$CH_2CH_3$, —$CH_2CH_2CH_3$, —$C_6H_6$, lower alkyl, aryl and substituted derivatives thereof.

2. Compound according to claim 1 wherein $R_1$ is —Z—$R_{11}$ with Z is O or S or S(O) or $S(O)_2$ and $R_{11}$ is —C(O)$R_{111}$ or —S(O)$R_{111}$ or —S(O)$_2R_{111}$.

3. Compound according to claim 2 wherein $R_1$ is —Z—$R_{11}$ and Z is O and $R_{11}$ is —C(O)H or —C(O)$CH_3$ and $R_2$ and $R_3$ are both —H or both the same as $R_{11}$.

4. Compound according to claim 2 wherein $R_1$ is —Z—$R_{11}$ and Z is S and $R_{11}$, $R_2$ and $R_3$ are —C(O)$CH_3$.

5. Method for the preparation of a compound according to claim 2 comprising contacting a compound of formula [2]

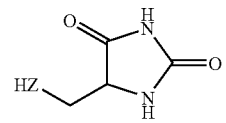

[2]

wherein Z is O or S
(a) with a compound of formula $R_{111}C(O)Y$
wherein $R_{111}$ is chosen from the list consisting of —H, —$CH_3$, —$CH_2X$, —$CHX_2$, —$CX_3$, —$C_6H_6$, —$C_6H_5X$, —$C_6H_4X_2$ lower alkyl and aryl,
wherein X represents Br, $CH_3$, $C_2H_5$, Cl, F or I and Y represents Br, Cl, F, I, OH or OC(O)$R_{111}$, or
(b) with a compound of formula $R_{111}S(O)_nY$
wherein n is 1 or 2,
wherein $R_{111}$ is chosen from the list consisting of —H, —$CH_3$, —$CH_2X$, —$CHX_2$, —$CX_3$, —$C_6H_6$, —$C_6H_5X$, —$C_6H_4X_2$ lower alkyl and aryl,
wherein X represents Br, $CH_3$, $C_2H_5$, Cl, F or I and Y represents Br, Cl, F, I, OH or OS(O)$_nR_{111}$.

6. Method according to claim 5 further comprising contacting the product obtained in (a) or (b) with an enamine of the general formula [3] or a ketoester of general formula [3a]

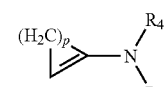

[3]

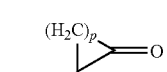

[3a]

wherein p has the value 1, 2, 3, 4, 5 or 6 and wherein $R_4$ and $R_5$ are independently chosen from the list consisting of —$CH_3$, —$CH_2CH_3$, —$CH_2CH_2CH_3$, —$C_6H_6$, lower alkyl, aryl or wherein $R_4$ and $R_5$ are connected to each other to form a ring chosen from the list consisting of —$CH_2CH_2$—, —$CH_2CH_2CH_2$—, —$CH_2CH_2CH_2CH_2$—, —$CH_2CH_2CH_2CH_2CH_2$— and —$CH_2ACH_2$— wherein A is —$(CH_2)_qO$—, —$(CH_2)_qS$—, —$(CH_2)_qS(O)$—, —$(CH_2)_qS(O)_2$— with q is 0, 1, 2, 3 or 4, and $R_7$ is chosen from the list consisting of —CH₃, —CH₂CH₃, —CH₂CH₂CH₃, —C₆H₆, lower alkyl, aryl and substituted derivatives thereof, followed by hydrolysis to give a compound of the general formula [4]

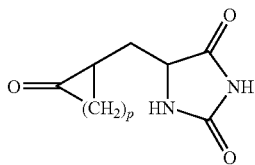
[4]

wherein p has the meaning as defined above.

7. Method according to claim 6 further comprising contacting said compound of general formula [4] with a hydantoinase, a carbamoylase and a hydantoin racemase to give a compound of the general formula [5]

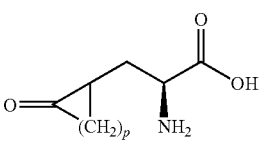
[5]

wherein p has the value 1, 2, 3, 4, 5 or 6.

8. Method according to claim 7 further comprising subjecting said compound of general formula [5] to hydrogenation to give a compound of the general formula [6]

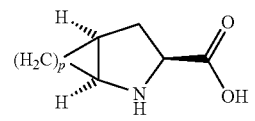
[6]

wherein p has the value 1, 2, 3, 4, 5 or 6.

9. Method according to claim 8 further comprising contacting said compound of general formula [6] with a compound of general formula [7] or a compound of general formula [8]

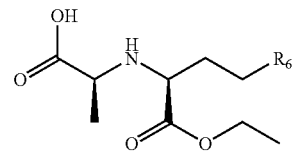
[7]

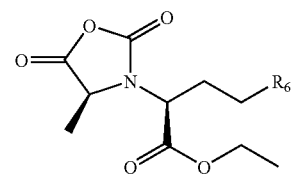
[8]

wherein R₆ is —CH₃ or phenyl, to give a compound of the general formula [9]

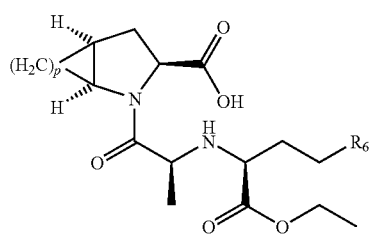
[9]

wherein p has the value 1, 2, 3, 4, 5 or 6.

10. Method according to claim 9 wherein R₆ is —CH₃ and p has the value 4 or wherein R₆ is phenyl and p has the value 3.

* * * * *